United States Patent [19]

Payne et al.

[11] Patent Number: 5,211,946
[45] Date of Patent: May 18, 1993

[54] BACILLUS THURINGIENSIS ISOLATES FOR CONTROLLING ACARIDES

[75] Inventors: Jewel M. Payne, San Diego, Calif.; Raymond J. C. Cannon; Angela L. Bagley, both of Sittingbourne, England

[73] Assignee: Mycogen Corporation, San Diego, Calif.

[21] Appl. No.: 768,141

[22] Filed: Sep. 30, 1991

Related U.S. Application Data

[63] Continuation-in-part of Ser. No. 759,248, Sep. 13, 1991, abandoned.

[51] Int. Cl.⁵ .................... A01N 61/00; C12N 1/20; C07K 15/02
[52] U.S. Cl. .................... 424/93 L; 424/405; 424/93 K; 424/93 D; 435/252.5; 435/832; 514/2; 530/350; 530/825; 935/64; 935/63
[58] Field of Search ................ 424/93 L, 405; 435/252.5, 252.31, 832; 935/64, 63; 530/350, 83 K, 83 D; 514/2

[56] References Cited

U.S. PATENT DOCUMENTS

| | | | |
|---|---|---|---|
| 4,695,455 | 9/1987 | Barnes et al. | 424/93 D |
| 4,771,131 | 9/1988 | Herrnstadt et al. | 536/27 |
| 4,849,217 | 7/1989 | Soares et al. | 424/93 L |

OTHER PUBLICATIONS

Couch, T. L., (1980) "Mosquito Pathogenicity of *Bacillus thuringiensis* var. israelensis," Developments in Industrial Microbiology, 22:61–67.

Beegle, C. C. (1978) "Use of Entomogeneous Bacteria in Agroecosystems", Developments in Industrial Microbiology, 20:97–104.

Royalty, R. N., Hall, F. R. and Taylor, R. A. J. (1990). Effects of thuringiensis on *Tetranychus urticae* (Acari: Tetranychidae) mortality, fucundity and feeding J. Econ. Entomol. 83:792–798.

Neal, J. W. Lingquist, R. K., Gott, K. M. and Casey, M. L. (1987) "Activity of the thermostable beta–exotoxin of *Bacillus thuringiensis* Berliner on *Tetranychus urticae* and *Tetranychus cinnabarinus*", J. Agric. Entomol. 4:33–40.

Vlayen, P., Impe, G. and Van Semaille, R. (1978) "Effect of a commercial preparation of *Bacillus thuringiensis* on the spider mit *Tetranychus urticae* Koch. (Acari: Tetranychidae)" Mededelingen 43:471–479.

Hickman, C. P. 1973 in: *Biology of the Invertebrates*, C. V. Mosbey Co., St. Louis, pp. 497–499.

Hall et al. 1971 J. Invert Pathol. 18, 359–362.

*Primary Examiner*—Christopher S. F. Low
*Attorney, Agent, or Firm*—Saliwanchik & Saliwanchik

[57] ABSTRACT

Disclosed and claimed are *Bacillus thuringiensis* isolates designated B.t. PS45B1, B.t. PS24J, B.t. PS94R3 B.t. PS17, B.t. PS62B1 and B.t. PS74G1 which are active against acarid pests. Thus, these isolates, or mutants thereof, can be used to control such pests. Further, genes encoding novel δ-endotoxins can be removed from these isolates and transferred to other host microbes, or plants. Expression of the δ-endotoxins in microbe hosts results in the control of acarid pests, whereas transformed plants become resistant to acarid pests.

20 Claims, 1 Drawing Sheet

BACILLUS THURINGIENSIS ISOLATES FOR CONTROLLING ACARIDES

CROSS-REFERENCE TO A RELATED APPLICATION

This is a continuation-in-part of co-pending application Ser. No. 07/759,248, filed Sep. 13, 1991, now abandoned.

BACKGROUND OF THE INVENTION

The spore-forming microorganism *Bacillus thuringiensis* (B.t.) produces the best-known insect toxin. The toxin is a protein, designated as δ-endotoxin. It is synthesized by the B.t. sporulating cell. The toxin, upon being ingested in its crystalline form by susceptible insect larvae, is transformed into biologically active moieties by the insect gut juice proteases. The primary target is insect cells of the gut epithelium, which are rapidly destroyed. Experience has shown that the activity of the B.t. toxin is so high that only nanogram amounts are required to kill susceptible insects.

The reported activity spectrum of B.t. covers insect species within the order Lepidoptera, which is a major insect problem in agriculture and forestry. The activity spectrum also includes the insect order Diptera, wherein reside mosquitoes and blackflies. See Couch, T. L., (1980) "Mosquito Pathogenicity of *Bacillus thuringiensis* var. israelensis," Developments in Industrial Microbiology, 22:61-67; Beegle, C. C., (1978) "Use of Entomogeneous Bacteria in Agroecosystems," Developments in Industrial Microbiology, 20:97-104.

U.S. Pat. No. 4,771,131 discloses a toxin gene isolated from a strain of *Bacillus thuringiensis*. This gene encodes a toxin which is active against beetles of the order Coleoptera.

There have been published reports concerning the use of *Bacillus thuringiensis* preparations for the control of mites. These publications are as follow:

Royalty, R. N., Hall, F. R. and Taylor, R. A. J. 1990. Effects of thuringiensin on *Tetranychus urticae* (Acari: Tetranychidae) mortality, fecundity, and feeding. J. Econ. Entomol. 83:792-798.

Neal, J. W., Lindquist, R. K., Gott, K. M. and Casey, M. L. 1987. Activity of the themostable beta-exotoxin of *Bacillus thuringiensis* Berliner on *Tetranychus urticae* and *Tetranychus cinnabarinus*. J. Agric. Entomol. 4:33-40.

Vlayen, P., Impe, G. and Van Semaille, R. 1978. Effect of a commercial preparation of *Bacillus thuringiensis* on the spider mite *Tetranychus urticae* Koch. (Acari: Tetranychidae). Mededelingen 43:471-479.

In the above published studies, the active ingredient in the B.t. preparations was beta-exotoxin (also called thuringiensin).

U.S. Pat. No. 4,695,455 concerns methods and compositions for preparing and using biological pesticides, where the pesticides are encapsulated in non-proliferating cells.

U.S. Pat. No. 4,849,217 concerns B.t. isolates active against the alfalfa weevil.

BRIEF SUMMARY OF THE INVENTION

The subject invention concerns *Bacillus thuringiensis* isolates which have acaricidal properties. Unlike published reports of the use of B.t. β-exotoxins to control mites, the subject invention isolates express δ-endotoxins which control mites. The use of δ-endotoxins is highly advantageous in view of the known general toxicity of β-exotoxins to humans and animals.

More specifically, the subject invention concerns *Bacillus thuringiensis* isolates designated B.t. PS45B1, B.t. PS24J, B.t. PS94R3, B.t. PS17, B.t. PS62B1 and B.t. PS74G1.

The B.t. isolates of the subject invention are toxic to the Two Spotted Spider Mite, *Tetranychus urticae*. Thus, these isolates can be used to control this mite. Further, the δ-endotoxins from these B.t. isolates can be isolated by standard procedures, e.g. ion exchange, and formulated by standard procedures to control the Two Spotted Spider Mite. These B.t. isolates can also be used against non-phytophagus mites such as acarid pests of livestock, fowl and stored products. Still further, the gene(s) from the B.t. isolates of the invention which encode the acaricidal toxin can be cloned from the isolates and then used to transform other hosts, e.g., prokaryotic, eukaryotic or plants, which transformed host can be used to control mites, or, in the case of transgenic plants, be resistant to mites.

DETAILED DISCLOSURE OF THE INVENTION

Figure 1A:
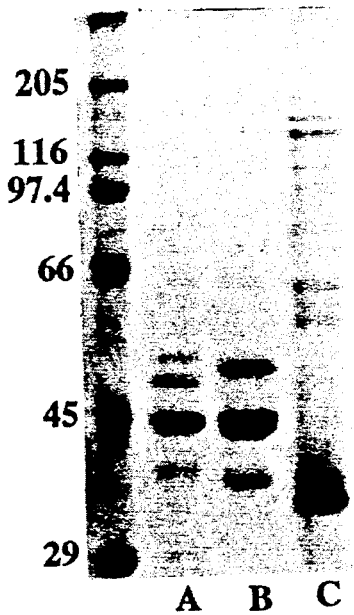
FIG. 1A is a photograph of a 12% SDS polyacrylamide gel showing alkali-soluble proteins of three isolates of the subject invention. Lane A: *Bacillus thuringiensis* PS24J; Lane B: *Bacillus thuringiensis* PS94R3; Lane C: *Bacillus thuringiensis* PS45B1.
Figure 1B:
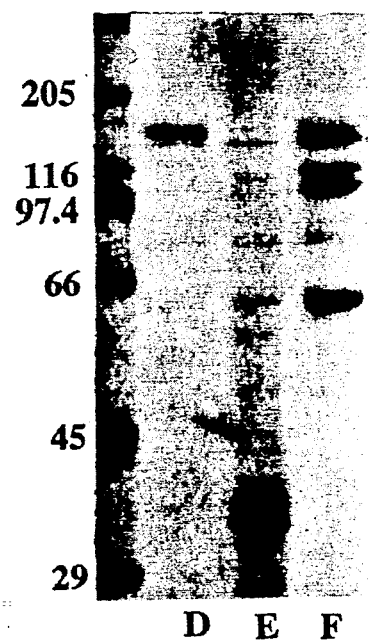
FIG. 1B is a photograph of a 12% SDS polyacrylamide gel showing alkali-soluble proteins of three isolates of the invention. Lane D: *Bacillus thuringiensis* PS17; Lane E: *Bacillus thuringiensis* PS62B1; Lane F: *Bacillus thuringiensis* PS74C1.

Upon applying an acaricidal-effective amount of a microbe, or toxin, as disclosed herein, in a suitable acaricidal formulation to the environment of the target pest, there is obtained effective control of these pests. An acaricidal-effective amount can vary from about 1 to about 12 l/ha, depending upon the nature and quantity of the pests to be controlled, the time of year, temperature, humidity, and other known factors which may affect a bioinsecticide. It is well within the skill of those trained in this art to determine the quantity of bioinsecticide to apply in order to obtain effective control of target pests.

The intracellular δ-endotoxin protein can be combined with other insecticidal proteins (including those obtained from sources other than *Bacillus thuringiensis*) to increase the spectrum of activity to give complete control of target pests.

The B.t. cells may be formulated in a variety of ways. They may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, gels, suspensions, emulsifiable concentrates, or the like. The ingredients may include rheological agents, surfactants, emulsifiers, dispersants, or polymers.

The pesticidal concentration will vary widely depending upon the nature of the particular formulation, particularly whether it is a concentrate or to be used directly. The pesticide will be present in at least 1% by weight and may be 100% by weight. The dry formulations will have from about 1–95% by weight of the pesticide while the liquid formulations will generally be from about 1–60% by weight of the solids in the liquid phase. The formulations will generally have from about $10^2$ to about $10^4$ cells/mg. These formulations will be administered at about 50 mg (liquid or dry) to 1 kg or more per hectare.

The formulations can be applied to the environment of the target pest(s), e.g., plants, livestock, fowl, soil or water, by spraying, dusting, sprinkling, or the like.

The B.t. isolates of the invention have the following characteristics:

| Strain | Crystal Type | Approx. Mol. Wt. of Proteins (kDa) |
|---|---|---|
| *B. thuringiensis* PS24J | Long | 51, 48, 43 |
| *B. thuringiensis* PS94R3 | Long | 50, 43, 42 |
| *B. thuringiensis* PS45B1 | Multiple | 150, 135, 35 |
| *B. thuringiensis* PS17 | Long | 155, 145, 128 |
| *B. thuringiensis* PS62B1 | Attached multiple | 35 |
| *B. thuringiensis* PS74G1 | Amorphic | 148, 112, 104, 61 |

Additionally, the isolates have the following common characteristics:

Colony morphology—large colony, dull surface, typical B.t.

Vegetative cell morphology—typical B.t.

The B.t. isolates of the invention, and mutants thereof, can be cultured using standard known media and fermentation techniques. Upon completion of the fermentation cycle, the bacteria can be harvested by first separating the B.t. spores and crystals from the fermentation broth by means well known in the art. The recovered B.t. spores and crystals can be formulated into a wettable powder, a liquid concentrate, granules or other formulations by the addition of surfactants, dispersants, inert carriers and other components to facilitate handling and application for particular target pests. The formulation and application procedures are all well known in the art and are used with commercial strains. The novel B.t. isolates, and mutants thereof, can be used to control target pests.

The cultures of the subject invention were deposited in the Agricultural Research Service Patent Culture Collection (NRRL), Northern Regional Research Center, 1815 North University Street, Peoria, Ill. 61604 U.S.A.

| Culture | Accession No. | Deposit Date |
|---|---|---|
| *B.t.* PS45B1 | NRRL B-18396 | August 16, 1988 |
| *B.t.* PS24J | NRRL B-18881 | August 30, 1991 |
| *B.t.* PS94R3 | NRRL B-18882 | August 30, 1991 |
| *B.t.* PS17 | NRRL B-18243 | July 28, 1987 |
| *B.t.* PS62B1 | NRRL B-18398 | August 16, 1988 |
| *B.t.* PS74G1 | NRRL B-18397 | August 16, 1988 |

The subject cultures have been deposited under conditions that assure that access to the cultures will be available during the pendency of this patent application to one determined by the Commissioner of Patents and Trademarks to be entitled thereto under 37 CFR 1.14 and 35 U.S.C. 122. These deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of a deposit, and in any case, for a period of at least thirty (30) years after the date of deposit or for the enforceable life of any patent which may issue disclosing a culture. The depositor acknowledges the duty to replace a deposit should the depository be unable to furnish a sample when requested, due to the condition of a deposit. All restrictions on the availability to the public of the subject culture deposits will be irrevocably removed upon the granting of a patent disclosing them.

The toxin genes harbored by the novel isolates of the subject invention can be introduced into a wide variety of microbial hosts. Expression of the toxin gene results, directly or indirectly, in the intracellular production and maintenance of the pesticide. With suitable hosts, e.g., Pseudomonas, the microbes can be applied to the situs of mites where they will proliferate and be ingested by the mites. The result is a control of the mites. Alternatively, the microbe hosting the toxin gene can be treated under conditions that prolong the activity of the toxin produced in the cell. The treated cell then can be applied to the environment of the target pest. The resulting product retains the toxicity of the B.t. toxin.

Where the B.t. toxin gene is introduced via a suitable vector into a microbial host, and said host is applied to the environment in a living state, it is essential that certain host microbes be used. Microorganism hosts are selected which are known to occupy the "phytosphere"(phylloplane, phyllosphere, rhizosphere, and/or rhizoplane) of one or more crops of interest. These microorganisms are selected so as to be capable of successfully competing in the particular environment (crop and other insect habitats) with the wild-type microorganisms, provide for stable maintenance and expression of the gene expressing the polypeptide pesticide, and, desirably, provide for improved protection of the pesticide from environmental degradation and inactivation.

A large number of microorganisms are known to inhabit the phylloplane (the surface of the plant leaves) and/or the rhizosphere (the soil surrounding plant roots). These microorganisms include bacteria, algae, and fungi. Of particular interest are microorganisms, such as bacteria, e.g., genera Bacillus, Pseudomonas, Erwinia, Serratia, Klebsiella, Xanthomonas, Streptomyces, Rhizobium, Rhodopseudomonas, Methylophilius, Agrobacterium, Acetobacter, Lactobacillus, Arthrobacter, Azotobacter, Leuconostoc, Alcaligenes and Clostridium; fungi, particularly yeast, e.g., genera Saccharomyces, Cryptococcus, Kluyveromyces, Sporobolomyces, Rhodotorula, and Aureobasidium; microalgae, e.g., families Cyanophyceae, Prochlorophyceae, Rhodophyceae, Dinophyceae, Chrysophyceae, Prymnesiophyceae, Xanthophyceae, Raphidophyceae, Bacillariophyceae, Eustigmatophyceae, Cryptophyceae, Euglenophyceae, Prasinophyceae, and Chlorophyceae. Of particular interest are such phytosphere bacterial species as *Pseudomonas syringae. Pseudomonas fluorescens, Serratia marcescens, Acetobacter* xylinum, *Agrobacterium tumefaciens, Rhodopseudomonas spheroides, Xanthomonas campestris, Rhizobium melioti, Alcaligenes entrophus,* and *Azotobacter vinlandii*; and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae,* and *Aureobasidium pollulans.* Of particular interest are the pigmented microorganisms.

A wide variety of ways are available for introducing a B.t. gene expressing a toxin into the microorganism host under conditions which allow for stable maintenance and expression of the gene. One can provide for DNA constructs which include the transcriptional and translational regulatory signals for expression of the toxin gene, the toxin gene under their regulatory control and a DNA sequence homologous with a sequence in the host organism, whereby integration will occur, and/or a replication system which is functional in the host, whereby integration or stable maintenance will occur.

The transcriptional initiation signals will include a promoter and a transcriptional initiation start site. In some instances, it may be desirable to provide for regulative expression of the toxin, where expression of the toxin will only occur after release into the environment. This can be achieved with operators or a region binding to an activator or enhancers, which are capable of induction upon a change in the physical or chemical environment of the microorganisms. For example, a temperature sensitive regulatory region may be employed, where the organisms may be grown up in the laboratory without expression of a toxin, but upon release into the environment, expression would begin. Other techniques may employ a specific nutrient medium in the laboratory, which inhibits the expression of the toxin, where the nutrient medium in the environment would allow for expression of the toxin. For translational initiation, a ribosomal binding site and an initiation codon will be present.

Various manipulations may be employed for enhancing the expression of the messenger RNA, particularly by using an active promoter, as well as by employing sequences, which enhance the stability of the messenger RNA. The transcriptional and translational termination region will involve stop codon(s), a terminator region, and optionally, a polyadenylation signal. A hydrophobic "leader" sequence may be employed at the amino terminus of the translated polypeptide sequence in order to promote secretion of the protein across the inner membrane.

In the direction of transcription, namely in the 5' to 3' direction of the coding or sense sequence, the construct will involve the transcriptional regulatory region, if any, and the promoter, where the regulatory region may be either 5' or 3' of the promoter, the ribosomal binding site, the initiation codon, the structural gene having an open reading frame in phase with the initiation codon, the stop codon(s), the polyadenylation signal sequence, if any, and the terminator region. This sequence as a double strand may be used by itself for transformation of a microorganism host, but will usually be included with a DNA sequence involving a marker, where the second DNA sequence may be joined to the toxin expression construct during introduction of the DNA into the host.

By a marker is intended a structural gene which provides for selection of those hosts which have been modified or transformed. The marker will normally provide for selective advantage, for example, providing for biocide resistance, e.g., resistance to antibiotics or heavy metals; complementation, so as to provide prototropy to an auxotrophic host, or the like. Preferably, complementation is employed, so that the modified host may not only be selected, but may also be competitive in the field. One or more markers may be employed in the development of the constructs, as well as for modifying the host. The organisms may be further modified by providing for a competitive advantage against other wild-type microorganisms in the field. For example, genes expressing metal chelating agents, e.g., siderophores, may be introduced into the host along with the structural gene expressing the toxin. In this manner, the enhanced expression of a siderophore may provide for a competitive advantage for the toxin-producing host, so that it may effectively compete with the wild-type microorganisms and stably occupy a niche in the environment.

Where no functional replication system is present, the construct will also include a sequence of at least 50 basepairs (bp), preferably at least about 100 bp, and usually not more than about 5000 bp of a sequence homologous with a sequence in the host. In this way, the probability of legitimate recombination is enhanced, so that the gene will be integrated into the host and stably maintained by the host. Desirably, the toxin gene will be in close proximity to the gene providing for complementation as well as the gene providing for the competitive advantage. Therefore, in the event that a toxin gene is lost, the resulting organism will be likely to also lose the complementing gene and/or the gene providing for the competitive advantage, so that it will be unable to compete in the environment with the gene retaining the intact construct.

A large number of transcriptional regulatory regions are available from a wide variety of microorganism hosts, such as bacteria, bacteriophage, cyanobacteria, algae, fungi, and the like. Various transcriptional regulatory regions include the regions associated with the trp gene, lac gene, gal gene, the lambda left and right promoters, the tac promoter, the naturally-occurring promoters associated with the toxin gene, where functional in the host. See for example, U.S. Pat. Nos. 4,332,898, 4,342,832 and 4,356,270. The termination region may be the termination region normally associated with the transcriptional initiation region or a different transcriptional initiation region, so long as the two regions are compatible and functional in the host.

Where stable episomal maintenance or integration is desired, a plasmid will be employed which has a replication system which is functional in the host. The replication system may be derived from the chromosome, an episomal element normally present in the host or a different host, or a replication system from a virus which is stable in the host. A large number of plasmids are available, such as pBR322, pACYC184, RSF1010, pRO1614, and the like. See for example, Olson et al., (1982) J. Bacteriol. 150:6069, and Bagdasarian et al., (1981) Gene 16:237, and U.S. Pat. Nos. 4,356,270, 4,362,817, and 4,371,625.

The B.t. gene can be introduced between the transcriptional and translational initiation region and the transcriptional and translational termination region, so as to be under the regulatory control of the initiation region. This construct will be included in a plasmid, which will include at least one replication system, but may include more than one, where one replication system is employed for cloning during the development of the plasmid and the second replication system is necessary for functioning in the ultimate host. In addition, one or more markers may be present, which have been described previously. Where integration is desired, the plasmid will desirably include a sequence homologous with the host genome.

The transformants can be isolated in accordance with conventional ways, usually employing a selection technique, which allows for selection of the desired organism as against unmodified organisms or transferring organisms, when present. The transformants then can be tested for pesticidal activity.

Suitable host cells, where the pesticide-containing cells will be treated to prolong the activity of the toxin in the cell when the then treated cell is applied to the environment of target pest(s), may include either prokaryotes or eukaryotes, normally being limited to those cells which do not produce substances toxic to higher organisms, such as mammals. However, organisms which produce substances toxic to higher organisms could be used, where the toxin is unstable or the level of application sufficiently low as to avoid any possibility of toxicity to a mammalian host. As hosts, of particular interest will be the prokaryotes and the lower eukaryotes, such as fungi, as disclosed previously.

Characteristics of particular interest in selecting a host cell for purposes of production include ease of introducing the B.t. gene into the host, availability of expression systems, efficiency of expression, stability of the pesticide in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; survival in aqueous environments; lack of mammalian toxicity; attractiveness to pests for ingestion; ease of killing and fixing without damage to the toxin; and the like. Other considerations include ease of formulation and handling, economics, storage stability, and the like.

The cell will usually be intact and be substantially in the proliferative form when treated, rather than in a spore form, although in some instances spores may be employed.

Treatment of the microbial cell, e.g., a microbe containing the B.t. toxin gene, can be by chemical or physical means, or by a combination of chemical and/or physical means, so long as the technique does not deleteriously affect the properties of the toxin, nor diminish the cellular capability in protecting the toxin. Examples of chemical reagents are halogenating agents, particularly halogens of atomic no. 17-80. More particularly, iodine can be used under mild conditions and for sufficient time to achieve the desired results. Other suitable techniques include treatment with aldehydes, such as formaldehyde and glutaraldehyde; anti-infectives, such as zephiran chloride and cetylpyridinium chloride; alcohols, such as isopropyl and ethanol; various histologic fixatives, such as Lugol iodine, Bouin's fixative, and Helly's fixative (See: Humason, Gretchen L., Animal Tissue Techniques, W. H. Freeman and Company, 1967); or a combination of physical (heat) and chemical agents that preserve and prolong the activity of the toxin produced in the cell when the cell is administered to the host animal. Examples of physical means are short wavelength radiation such as gamma-radiation and X-radiation, freezing, UV irradiation, lyophilization, and the like.

The cells generally will have enhanced structural stability which will enhance resistance to environmental conditions. Where the pesticide is in a proform, the method of inactivation should be selected so as not to inhibit processing of the proform to the mature form of the pesticide by the target pest pathogen. For example, formaldehyde will crosslink proteins and could inhibit processing of the proform of a polypeptide pesticide. The method of inactivation or killing retains at least a substantial portion of the bio-availability or bioactivity of the toxin.

The cellular host containing the B.t. insecticidal gene may be grown in any convenient nutrient medium, where the DNA construct provides a selective advantage, providing for a selective medium so that substantially all or all of the cells retain the B.t. gene. These cells may then be harvested in accordance with conventional ways. Alternatively, the cells can be treated prior to harvesting.

The B.t. cells of the invention can be cultured using standard art media and fermentation techniques. Upon completion of the fermentation cycle the bacteria can be harvested by first separating the B.t. spores and crystals from the fermentation broth by means well known in the art. The recovered B.t. spores and crystals can be formulated into a wettable powder, liquid concentrate, granules or other formulations by the addition of surfactants, dispersants, inert carriers, and other components to facilitate handling and application for particular target pests. These formulations and application procedures are all well known in the art.

Formulated bait granules containing an attractant and spores and crystals of the B.t. isolates, or recombinant microbes comprising the gene(s) obtainable from the B.t. isolates disclosed herein, can be applied to the soil or in the vicinity of stored products. Formulated product can also be applied as a seed-coating or root treatment or total plant treatment at later stages of the crop cycle.

Mutants of the novel isolates of the invention can be made by procedures well known in the art. For example, an asporogenous mutant can be obtained through ethylmethane sulfonate (EMS) mutagenesis of a novel isolate. The mutants can be made using ultraviolet light and nitrosoguanidine by procedures well known in the art.

A smaller percentage of the asporogenous mutants will remain intact and not lyse for extended fermentation periods; these strains are designated lysis minus (−). Lysis minus strains can be identified by screening asporogenous mutants in shake flask media and selecting those mutants that are still intact and contain toxin crystals at the end of the fermentation. Lysis minus strains are suitable for a cell fixation process that will yield a protected, encapsulated toxin protein.

To prepare a phage resistant variant of said asporogenous mutant, an aliquot of the phage lysate is spread onto nutrient agar and allowed to dry. An aliquot of the phage sensitive bacterial strain is then plated directly over the dried lysate and allowed to dry. The plates are incubated at 30° C. The plates are incubated for 2 days and, at that time, numerous colonies could be seen growing on the agar. Some of these colonies are picked and subcultured onto nutrient agar plates. These apparent resistant cultures are tested for resistance by cross streaking with the phage lysate. A line of the phage lysate is streaked on the plate and allowed to dry. The presumptive resistant cultures are then streaked across the phage line. Resistant bacterial cultures show no lysis anywhere in the streak across the phage line after overnight incubation at 30° C. The resistance to phage is then reconfirmed by plating a lawn of the resistant culture onto a nutrient agar plate. The sensitive strain is also plated in the same manner to serve as the positive control. After drying, a drop of the phase lysate is plated in the center of the plate and allowed to dry. Resistant cultures showed no lysis in the area where the phage lysate has been placed after incubation at 30° C. for 24 hours.

Following are examples which illustrate procedures, including the best mode, for practicing the invention. These examples should not be construed as limiting. All percentages are by weight and all solvent mixture proportions are by volume unless otherwise noted.

EXAMPLE 1

Culturing of the B.t. Isolates

A subculture of the B.t. isolates, or mutants thereof, can be used to inoculate the following medium, a peptone, glucose, salts medium.

| | | |
|---|---|---|
| Bacto Peptone | 7.5 | g/l |
| Glucose | 1.0 | g/l |
| $KH_2PO_4$ | 3.4 | g/l |
| $K_2HPO_4$ | 4.35 | g/l |
| Salt Solution | 5.0 | ml/l |
| $CaCl_2$ Solution | 5.0 | ml/l |
| pH 7.2 | | |
| Salts Solution (100 ml) | | |
| $MgSO_4.7H_2O$ | 2.46 | g |
| $MnSO_4.H_2O$ | 0.04 | g |
| $ZnSO_4.7H_2O$ | 0.28 | g |
| $FeSO_4.7H_2O$ | 0.40 | g |
| $CaCl_2$ Solution (100 ml) | | |
| $CaCl_2.2H_2O$ | 3.66 | g |

The salts solution and $CaCl_2$ solution are filter-sterilized and added to the autoclaved and cooked broth at the time of inoculation. Flasks are incubated at 30° C. on a rotary shaker at 200 rpm for 64 hr.

The above procedure can be readily scaled up to large fermentors by procedures well known in the art.

The B.t. spores and/or crystals, obtained in the above fermentation, can be isolated by procedures well known in the art. A frequently-used procedure is to subject the harvested fermentation broth to separation techniques, e.g., centrifugation.

EXAMPLE 2

Activity of B.t. Isolates Against Mites

All *B. thuringiensis* isolates of the invention were tested as spray-dried powders of fermentation broths which were concentrated by centrifugation. Pellets, which consist of water and biomass (spores, crystalline delta-endotoxins, cellular debris and growth media) were mixed with a standard carrier, preservative and surfactant. Powders, which consisted of 25% biomass, were made using a Yamato spray drier. (Sold by Yamato Scientific Co., Ltd. Tokoyo, Japan)

All broths were tested for the presence of beta-exotoxin by a larval house fly bioassay (Campbell, D. P., Dieball, D. E. and Brackett, J. M., 1987, Rapid HPLC assay for the β-exotoxin of *Bacillus thuringiensis*. J. Agric. Food Chem. 35:156-158). Only isolates which tested free of β-exotoxin were used in the assays against mites.

*B. thuringiensis* isolates were tested using an artificial feeding assay. Spray-dried powders were prepared for testing by mixing 25 mg of powder in 5 ml of a 10% sucrose solution. This mixture was then sonicated for 8 min to produce a suspension.

Two ml of suspension was placed in a reservoir consisting of a metal ring with a Parafilm TM M film bottom. A petri dish containing approximately 30 female Two-spotted spider mites (*Tetranychus urticae*) was placed on the underside of the film. Mites were allowed to feed on the sucrose solution for 24 hrs and then transfered to 2 cm French bean leaf discs (20 mites per disc). Mortality was determined after 7 days (Table 1). Each assay was done in triplicate.

TALBE 1

Toxicity of *Bacillus thuringiensis* isolates to the two spotted spider mite, *Tetranychus urticae*. Mortality was determined after 7 days of treatment.

| Isolate | Percent Mortality |
|---|---|
| B.t. PS45B1 | 82 |
| B.t. PS24J | 90 |
| B.t. PS94R3 | 97 |
| B.t. PS17 | >90 |
| B.t. PS62B1 | >90 |
| B.t. PS74G1 | >90 |
| Control | 10 |

EXAMPLE 3

Insertion of Toxin Genes Into Plants

The genes coding for the insecticidal toxins, as disclosed herein, can be inserted into plant cells using the Ti plasmid from *Agrobacter tumefaciens*. Plant cells can then be caused to regenerate into plants (Zambryski, P., Joos, H., Gentello, C., Leemans, J., Van Montague, M. and Schell, J [1983] Cell 32:1033-1043). A particularly useful vector in this regard is pEND4K (Klee, H. J., Yanofsky, M. F. and Nester, E. W. [1985] Bio/Technology 3:637-642). This plasmid can replicate both in plant cells and in bacteria and has multiple cloning sites for passenger genes. The toxin gene, for example, can be inserted into the BamHI site of pEND4K, propagated in *E. coli*, and transformed into appropriate plant cells. Transgenic cotton plants resistant to mites can be obtained by this or other known procedures.

EXAMPLE 4

Cloning of Bacillus thuringiensis Genes Into Baculoviruses

The genes coding for the insecticidal toxins, as disclosed herein, can be cloned into baculoviruses such as *Autographa californica* nuclear polyhedrosis virus (AcNPV). Plasmids can be constructed that contain the AcNPV genome cloned into a commercial cloning vector such as pUC8. The AcNPV genome is modified so that the coding region of the polyhedrin gene is removed and a unique cloning site for a passenger gene is placed directly behind the polyhedrin promoter. Examples of such vectors are pGP-B6874, described by Pennock et al. (Pennock, G. D., Shoemaker, C. and Miller, L. K. [1984] Mol. Cell. Biol. 4:399-406), and pAC380, described by Smith et al. (Smith, G. E., Summers, M. D. and Fraser, M. J. [1983] Mol Cell. Biol. 3:2156-2165). The genes coding for the protein toxins of the invention can be modified with BamHI linkers at appropriate regions both upstream and downstream from the coding region and inserted into the passenger site of one of the AcNPV vectors.

We claim:

1. A process for controlling acarid pests of livestock, fowl, and stored products, which comprises contacting said pests with an acarid-controlling effective amount of a *Bacillus thuringiensis* isolate selected from the group consisting of B.t. PS45B1, B.t. PS24J, B.t. PS94R3, B.t. PS17, B.t. PS62B1, and B.t. PS74G1, and mutants thereof, which retain the property of activity against acarid pests.

2. The process, according to claim 1, wherein said microbe is *Bacillus thuringiensis* PS45B1.

3. The process, according to claim 1, wherein said microbe is *Bacillus thuringiensis* PS24J.

4. The process, according to claim 1, wherein said microbe is *Bacillus thuringiensis* PS94R3.

5. The process, according to claim 1, wherein said microbe is *Bacillus thuringiensis* PS17.

6. The process, according to claim 1, wherein said microbe is *Bacillus thuringiensis* PS62B1.

7. The process, according to claim 1, wherein said microbe is *Bacillus thuringiensis* PS74G1.

8. A method for controlling acarid pests of livestock, fowl, and stored products, which comprises contacting said pests with an acarid-controlling effective amount of a stable lysis− spo− cry+ *Bacillus thuringiensis* isolate selected from the group consisting of B.t. PS45B1, B.t. PS24J, B.t. PS94R3, B.t. PS17, B.t. PS62B1 and B.t. PS74G1, and mutants thereof, which retain the property of activity against acarid pests.

9. The process, according to claim 1, wherein said acarid pest is a mite.

10. The process, according to claim 9, wherein said mite is the Two Spotted Spider Mite.

11. A composition of matter comprising a *Bacillus thuringiensis* isolate selected from the group consisting of B.t. PS24J, and B.t. PS94R3, and mutants thereof, which retain the property of activity against acarid pests in association with an inert carrier.

12. The composition of matter, according to claim 11, comprising *Bacillus thuringiensis* PS24J.

13. The composition of matter, according to claim 11, comprising *Bacillus thuringiensis* PS94R3.

14. A pesticidal composition comprising substantially intact, treated *Bacillus thuringiensis* cells having prolonged pesticidal activity and greater persistence in the feeding zone when applied to the environment of acarid pests, wherein said pesticide is a polypeptide toxic to acarid pests, is intracellular, and is produced by a *Bacillus thuringiensis* isolate selected from the group consisting of B.t. PS24J, and B.t. PS94R3, and mutants thereof, which retain the property of activity against acarid pests.

15. The pesticidal composition, according to claim 14, wherein said treated cells are treated by chemical or physical means to prolong the pesticidal activity in the environment.

16. A toxin encoded by a gene from a *Bacillus thuringiensis* isolate selected from the group consisting of B.t. PS24J, and B.t. PS94R3, and mutants thereof, which retain the property of activity against acarid pests, wherein said toxin is active against acarid pests.

17. A biologically pure culture of *Bacillus thuringiensis* selected from the group consising of B.t. PS94J, and B.t. PS94R3, and mutants thereof, which retain the property of activity against acarid pests.

18. The process, according to claim 1, wherein toxic crystals from said isolates are used in the process.

19. The method, according to claim 8, wherein toxic crystals from said isolates are used in the method.

20. The composition, according to claim 11, which comprises toxin crystals from said isolates.

* * * * *

UNITED STATES PATENT AND TRADEMARK OFFICE
CERTIFICATE OF CORRECTION

PATENT NO. : 5,211,946

DATED : May 18, 1993

INVENTOR(S) : Jewel Payne, Raymond J.C. Cannon and Angela L. Bagley

It is certified that error appears in the above-indentified patent and that said Letters Patent is hereby corrected as shown below:

Column 11   line 30: Delete "lysis_spo_cry+" and insert --lysis⁻spo⁻cry⁺--.

Column 12   line 30: Delete "*B.t.* PS94J" and insert --*B.t.* PS24J--.

Signed and Sealed this

First Day of February, 1994

Attest:

BRUCE LEHMAN

Attesting Officer    Commissioner of Patents and Trademarks